United States Patent [19]

Kravchenko

[11] Patent Number: 4,801,444
[45] Date of Patent: Jan. 31, 1989

[54] MEDICINAL PREPARATION FOR INDIVIDUAL PREVENTION OF VENEREAL DISEASES AND TREATMENT OF UROGENITAL TRICHOMONIASIS

[75] Inventor: Vladimir G. Kravchenko, Poltava, U.S.S.R.

[73] Assignee: Poltavsky Meditsinsky Stomatologichesky Institut, Poltava, U.S.S.R.

[21] Appl. No.: 164,059

[22] Filed: Mar. 3, 1988

[51] Int. Cl.$^4$ ................................................ A61L 9/04
[52] U.S. Cl. ........................................ 424/45; 514/701;
514/708; 514/699; 514/332; 514/646; 514/931;
514/934; 514/967; 514/969; 568/425; 568/448;
568/459; 424/430; 424/43
[58] Field of Search ............... 514/332, 258, 701, 708,
514/699, 646, 931, 934, 967, 969; 424/430, 318,
43, 45; 568/425, 448, 459

[56] References Cited

U.S. PATENT DOCUMENTS

| | | | |
|---|---|---|---|
| 3,390,186 | 6/1968 | Normant | 568/448 |
| 3,457,314 | 7/1969 | Siedel | 568/425 |
| 3,515,671 | 6/1970 | Adams | 514/699 |
| 3,594,468 | 7/1971 | Saurino | 424/430 |
| 3,743,727 | 11/1970 | Herschler | 514/708 |
| 3,932,642 | 1/1976 | Woitun | 514/258 |
| 4,196,151 | 4/1980 | Suyama | 568/459 |
| 4,525,480 | 6/1985 | Berke | 514/701 |
| 4,621,090 | 11/1986 | Iwata | 514/332 |

FOREIGN PATENT DOCUMENTS

| | | | |
|---|---|---|---|
| 7224274 | 8/1974 | Australia | 514/701 |
| 105448A | 8/1984 | European Pat. Off. | 424/318 |

*Primary Examiner*—Thurman K. Page
*Assistant Examiner*—Penny Prater
*Attorney, Agent, or Firm*—Burgess, Ryan & Wayne

[57] ABSTRACT

A medicinal preparation for individual prevention of venereal diseases and treatment of urogenital trichomoniasis comprises an efficient quantity of an active principle which is essentially a synergistic mixture of para-nitro-alpha-chlorocinnamic aldehyde of the formula:

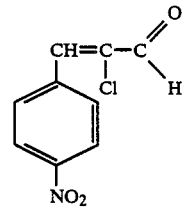

dimethylsulphoxide and a pharmaceutical excipient. Polyethyleneglycol having a molecular mass of 400 is recommended to be used as the pharmaceutical excipient.

A method for treatment of urogenital trichomoniasis consists in application of the medicinal preparation in question to the mucosa of human genitalia in a dose of 1.5 to 10 ml twice a day for 5 to 7 days.

9 Claims, No Drawings

MEDICINAL PREPARATION FOR INDIVIDUAL PREVENTION OF VENEREAL DISEASES AND TREATMENT OF UROGENITAL TRICHOMONIASIS

FIELD OF THE INVENTION

The present invention relates generally to medicine and more specifically it concerns a medicinal preparation for individual prevention of venereal diseases and treatment of urogenital trichomoniasis.

The herein-proposed medicinal preparation will find application in dermatovenereological and gynecological practice.

BACKGROUND OF THE INVENTION

At present a number of medicines are in widespread use in medicine for individual prevention of venereal diseases, such as silver-containing drugs, potassium permanganate, and mercury preparations, e.g., mercury dichloride solution, mercury subchloride ointment and Dublosan ointment. With the purpose of preventing syphilis and gonorrhea a medicinal preparation Oxyviridol has been suggested, consisting of 0.035 mass percent mercuric oxycyanide and 50 mass percent green soap in glycerine (cf. 'Medical prescription reference book' compiled by M. Kh. Bergolts, 1952, Medgiz Publishers, Moscow). However, the aforementioned drug possesses inadequate bactericidal potency against syphilis and gonorrhea pathogens, produces a considerable irritating effect on urethral mucosa, causes desquamation and lysis of the epithelial lining, and is therefore unsafe in clinical uses. The medical preparations mentioned above fail to find extensive application due to their inadequate reliability, whereas mercury-based drugs cannot be guaranteed as safe for human organism.

There has been proposed within recent years a 0.05–0.1 percent solution of Chlorhexidine (Hibitane) as a preventive of venereal diseases. The drug possesses an adequate bactericidal activity in experiments in vitro and in tests on animals (cf. 'The dermatology and venereology herald', No. 6, 1978, Moscow, On personal prevention of venereal diseases by I. M. Ovchinnikov et al., p. 49 (in Russian). However, clinical application of the aforesaid drug is accompanied by an irritating and withering effect upon the skin and genital mucosa in man. Besides, industrial production of Hibitane is a complicated and highly labour-consuming task.

Applied for topical (external) treatment of urogenital trichomoniasis are boric acid, lapis, zinc sulphate, copper sulphate, laevomycetin, Acetarsol, and others. However, these drugs are insufficiently efficacious and fail therefore to find windspread application.

At the present time imidazole medicines are most efficient for treatment of the aforesaid disease, e.g., Tinidazole, Metronidazole and Trichopol. However, their clinical use is attended by ever increasing resistance of trichomonads to the action of these drugs, which in turn is responsible for relapsing of a specific process (up to 8.4 percent of all cases) and for the onset of posttrichomonal phenomena. The drugs may be causative of some side effects, and are contraindicated in cases of hemopoietic disturbances, or active CNS affections.

SUMMARY OF THE INVENTION

The present invention has for its object to provide a medicinal preparation for individual prevention of venereal diseases and treatment of trichomoniasis that would have a convenient form of issue by selecting such chemical compounds as an active principle that would impart high efficacy to the present medicinal preparation and at the same time prevent side effects upon its application.

The aforesaid object is accomplished by providing a medicinal preparation for individual prevention of venereal diseases and treatment of urogential trichomoniasis, comprising an active principle and a pharmaceutical excipient, which medicinal preparation, according to the invention, incorporates an efficient quantity of the active principle which is essentially a synergic mixture comprised of paranitro-alpha-chlorocinnamic aldehyde of the following formula:

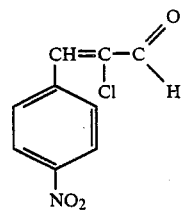

and dimethylsulphoxide.

Chemical compounds that make up the mixture proposed as an active principle, feature different modes of action which establish, in combination, the potentiating synergism which results in complete destruction of the protoplasm and cell membrane of the pathogens of syphilis, gonorrhea and trichomoniasis, thus imparting quickly expressed bactericidal and protistocidal effect to the medicinal preparation involved. The pathogens are disintegrated under the effect of the drug as fast as within the initial three minutes. The preparation possesses high efficacy both in prevention of venereal diseases and in treatment of urogenital trichomoniasis.

It is expedient to use polyethyleneglycol having a molecular mass of 400 as the pharmaceutical excipient, since it is toxic-free and proves to be an osmotically active substance promoting manifestation of the most biological potency in the active principle.

The drug comprising such an excipient produces no local irritating effect on skin and mucosa nor does it possess a systemically toxic or allergic action.

It is recommended that the present medicinal preparation be applied clinically in a liquid form with the following ratio of components (in mass percent):

| | |
|---|---|
| para-nitro-alpha-chlorocinnamic aldehyde of the aformentioned formula | 0.3 |
| dimethylsulphoxide | 5.0 |
| polyethyleneglycol with a molecular mass of 400 | to make up 100 |

Such a medicinal preparation features the most reliable preventive effect and possesses high antitrichomonal activity. A liquid medicinal form of the preparation enables its best contact with the pathogens that have got on the skin and mucosa.

It is recommended that the present medicinal preparation be applied for individual prevention of venereal diseases and treatment of urogenital trichomoniasis, particularly in women, in a liquid form dispensed in aerosol containers under pressure, its components being taken in the following ratio (in mass percent):

| | |
|---|---|
| para-nitro-alpha-chlorocinnamic aldehyde of the aforementioned formula | 0.3 |
| dimethylsulphoxide | 5.0 |
| polyethyleneglycol with a molecular mass of 400 | 20 to 30 |
| surfactant | 3.0 to 6.0 |
| water | to make up 100 | as well as a propellant in an amount of 3 to 10 percent of a total mass of the components.

Such a medicinal form makes it possible not only to provide an antivenereal effect whenever it becomes necessary but also enables female patients wanting treatment for urogenital trichomoniasis, to carry out therapeutic procedures by themselves.

There is also proposed a method for treatment of urogenital trichomoniasis, comprising application of the medicinal preparation, according to the invention, to human genital mucosa in a dose of 5 to 10 ml twice a day for 5 to 7 days.

Such a treatment method proves to be the most efficient in cases of uncomplicated urogenital trichomoniasis, though it is also applicable against ascending forms of trichomoniasis provided there is a necessary access for the medicinal preparation, according to the invention, to the affected area. Such a treatment method is attended by no side effects whatever, including those accompanied by local-irritating, systemically toxic or allergizing action.

DETAILED DESCRIPTION OF THE INVENTION

The herein-proposed medicinal preparation appears as a thick transparent liquid coloured from light yellow having a specific faint odour and stable when under storage in a light-protected place.

The drug may be dispensed in hermetically sealed 5 to 10 ml capacity flasks, or in aerosol containers.

The medicinal preparation for prevention of venereal diseases and treatment of trichomoniasis proposed according to the present invention is prepared by mixing the efficient amounts of para-nitro-alpha-chlorocinnamic aldehyde of the following formula:

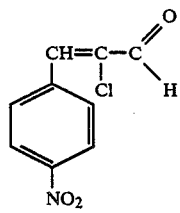

and dimethylsulphoxide till formation of a synergistic mixture in the form of a solution, followed by bringing the preparation to a preset concentration using a pharmaceutical excipient, viz., polyethyleneglycol having a molecular mass of 400, which has been selected due to its being excellently compatible with the active principles and low toxic. However, some other pharmaceutical excipients existing nowadays may be used for the purpose, such as glycerine, or propyleneglycol, 1,2-propanediol.

In order to obtain the medicinal preparation, according to the invention, in a liquid form under pressure dispensed in aerosol containers, added to the aforedescribed solution are a surfactant (3 to 6 mass percent) and water (to make up 100 mass percent), and the resultant solution is saturated, in an aerosol container, with a propellant taken in an amount of 3 to 10 percent of the total mass of the components. The amounts of the aforesaid substances are selected so that quickly destructable foam be produced upon application of the preparation.

The medicinal preparation, according to the invention, has been subjected to preclinical trials including investigation of its bactericidal and protistocidal potency in experiments in vitro and in tests with experimentally induced syphilis in rabbits; the drug has been studied for safety, including tests for local irritating effect, allergizing action, influence upon the immune system, as well as for some aspects of pharmacokinetics.

The preparation in question has been studied in concentration of 0.075, 0.15 and 0.3 percent. The concentration of the drug is determined according to the amount of para-nitro-alpha-chlorocinnamic aldehyde of the aforementioned formula, contained therein, with a constant quantitative content of dimethylsulphoxide (5 percent) and an equivalently-varying content of polyethyleneglycol having a molecular mass of 400. The drug has been studied for safety with a concentration of 0.3 percent.

In order to study the drug for gonococcocidal properties a pure gonococci culture is isolated from gonorrheal patients and seeded onto a great culture medium area (in matrasses). Then the 24-h culture is washed off from the matrasses with a sterile isotonic sodium-chloride solution, and a suspension is prepared from the obtained washing, containing one thousand millions of microbial bodies (according to the turbidimetric standard). The resultant suspension is dispensed in 0.5-ml sterile test tubes, whereupon added to each of them is 0.5 ml of the preparation under study having a doubled concentration so as to obtain a desired concentration under study after mixing the ingredients for 5 minutes. The mixture is then subjected to centrifugation at 1500 to 3000 rpm for 10 to 15 minutes to wash gonococci from the preparation. Then the supernatant liquid is removed and 1 ml of an isotonic sodium-chloride is added to the precipitate to obtain the initial volume, whereupon the mixture is centrifugated once more for repeated washing-off. The supernatant liquid is removed again, and the precipitate is seeded onto an agar-slant nutrient medium (ten test tubes with the nutrient medium per strain of the gonococcal culture). Then the test tubes containing the nutrient medium are placed in a temperature-controlled cabinet at 37° C. in an atmosphere with an increase content of carbon dioxide gas. The rate of growth of the gonococcal culture is determined every 24 hours within four days.

Taken as the control is a mixture of equal amounts of a suspension of the gonococcal culture and an isotonic sodium-chloride solution (0.5 ml each), which mixture is dispensed in test tubes, two times exposed to centrifugation (as in the test tubes of the experiment) and the precipitate is seeded onto a nutrient medium equivalent as to composition.

Used as a nutrient medium is plain (meat-infusion) agar prepared from rabbit meat and doped with casein hydrolysate, yeast autolysate, and preservative free large-cattle serum, as well as a lyophilic medium.

Studies into the effect of the medicinal preparation under consideration upon Treponema pallidum and vaginal trichomonads in experiments were carried out as follows.

Treponema pallidum was obtained from eight- or ten-day specific orchitis in rabbits and from patients affected by contagious forms of syphilis. There were studied tissue cultures of Nichols's strain and No. 8 strain of the Central dermatovenereological research institute (TsKVI). The cultures of vaginal trichomonads were isolated from patients suffering from urogenital trichomoniasis and grown on an artificial Johnson-Trussell medium.

The experimental procedure consisted in mixing equal volumes of a suspension of Treponema pallidum (or a culture of trichomonads) and the preparation under study, taken in a double concentration since the latter is reduced twofold upon mixing the ingredients. Then the native preparations are made from the resultant mixture and are exposed to microscopy in a darkened (for Treponema pallidum and Trichomonas), or a phase-contrast (for vaginal trichomonads) field of a microscope. Action of the preparation under test was judged by the degree and rate of its effect on the mobility and morphology of the pathogens. The effect was considered positive when complete motionlessness of the pathogens occurred at once, i.e., at the instant when the preparation was made, or within the following 3 to 5 minutes for Treponema pallidum and 5 to 10 minutes for trichomonads. The effect of the drug under test on the morphology of Treponema pallidum and Trichomonas was considered still more positive if the pathogens lost shape within the abovementioned period of time (i.e., the Treponuma pallidum pathogens became thinner, their spirals were smoothed out, some bulging individuals occurred, as well as debris, or the pathogens were lyzed completely; vaginal trichomonads lost their flagellas, got disintegrated and lyzed).

Another version of studies into the treponemicidal effect of the drug under test consisted in successively applying a droplet of the suspension of Treponema pallidum and a droplet of the medicine under test to the stage of a microscope, whereupon the mixture was carefully intermixed with the pointed end of a Pasteur pipette, covered with a cover glass and was immediately observed in a dark field of the microscope. Such a study made it possible to reveal the effect of the drug under test on treponemes as early as within the initial 20 to 30 seconds following the contact between the suspension and the drug. Served as the control of these tests was a mixture of equal volumes of a suspension of Treponema pallidum (from 20 to 30 up to 80 microorganisms in the field of the microscope, or of that of vaginal trichomonads and an isotonic sodium chloride solution. Microscopic specimens were examined in a dark field of the Biolam microscope and with the microscope available from Opton Co using a darkfield and a phase-contrast substage condenser, as well as objective lenses ($25 \times 0.45$; $40 \times 0.6$).

Studies in the preventive action of the drug in tests with experimentally induced syphilis were carried out on sexually mature well nourished 2.5 to 4 kg male rabbits of the various races and colours (chinchilla, white and silvery grey giant).

Before experiments all test rabbits had been under observation for at least one month so as to rule out spontaneous spirochetosis in the test animals. All the test rabbits were examined for syphilis with the use of a complex of serologic tests.

Preventive effect of the drug under test has been studied in two parallel running versions of tests with experimentally induced syphilis in rabbits.

The first version involved studies in the treponemicidal effect of the drug upon intracutaneous administration of a mixture of the suspension of Treponema pallidum and of the drug under test. With the purpose in view the test rabbits were fixed in a routine way and 0.75 ml of a mixture (equal volumes of the suspension of Treponema pallidum and the doubled concentration of the drug under test, since the concentration of the latter was reduced twofold upon mixing with the suspension) was injected intracutaneously in either of the scrotal halves.

The test animals of one of the groups were given the aforesaid mixture just after a ten-minute contact of the mixture of ingredients and their intermixing with a glass stick, while the test rabbits of the other group were administered the mixture after its having been centrifugalized and upon a ten-minute contact of a quantity of a sterile isotonic NaCl solution (washing off from the drug under test).

The aforediscussed studies were performed with a view to ruling out any possibility of inactivation (by precipitation) of the drug in a protein medium of the animals' organism and of destroying its bactericidal effect. Centrifugation of the suspension of Tremponema pallidum before its administration was aimed at determination of adequacy of the treponemicidal effect of the drug after its ten-minute action on pallid treponemes. The control rabbits were given intracutaneously in the scrotal region a mixture of equal volumes of a suspension of pallid treponemes and an isotonic NaCl solution.

The second, principal version of experiments involved those, wherein the syphilis infecting conditions of the test rabbits to some extent approximated routine syphilis infecting conditions in man. With that aim the animals were infected with a suspension of Treponeme pallidum in an isotonic NaCl solution by rubbing the suspension into the scarified scrotal skin. Preliminarily the scrotal skin was to be wiped with cotton wad wetted first in ethanol, then in ether. Then the scrotal skin is stretched to a maximum extent with the fingers of the experimenter's left hand, while the skin of the both scrotal halves was scarified by the experimenter's right hand using fine-grained emery paper. The scarified skin area should be 1 to 1.5 sq.cm and should appear as a rough surface showing some tissue fluid emerging as pin-points. Bleeding must be avoided. Then the freshly prepared suspension of the syphilitic pathogen containing 20 to 25 treponemes in the field of a microscope, was applied, in an amount of 0.1 ml, to the scarified areas of the scrotal skin and was rubbed with a sterile glass stick for 1 to 1.5 minutes. Next the scrotal skin was pinched with two Péan's forceps at a distance not shorter than 0.5 cm from the place of application of the inoculative material, and the two forceps were crossed together, thus establishing a skin fold which protects the treponemes against getting dried, so as to provide the best conditions for infecting (after S. T. Pavlov). The forceps remained crossed-together for 1 to 1.5 hours, whereupon they were removed.

The test rabbits were subjected to disinfecting treatment with the drug under trial in different periods of time after infecting (i.e., after 15 minutes, 1, 2, 3 hours). The treatment consisted in applying 0.1 ml of the drug under test to each of the infected scrotal skin areas and carefully rubbing it into the skin with a sterile glass spatula for 1 to 1.5 minutes. No disinfecting treatment was given to the control rabbits.

The test animals were observed for 4 to 12 months with weekly clinical examination and monthly serologic examination using a complex of serologic tests for syphilis, i.e., Wassermann reaction with cardiolopin lipoid and treponemal antigens, Kahh and Sachs-Witebsky precipitation tests, immunofluorescence test (RIF-10 and RIF-200), and microprecipitation test (RMP).

Reliability of preventive protection of the test rabbits against syphilis was judged by the absence of any clinical manifestations of the disease in the animals and by the negative serologic tests, as well as by the negative results of transplanting the popliteal lymph nodes from the test animals to the indicator rabbits in two successive (serial) passages. Considered as the final evidence of the drug preventive action were the positive results of reinoculation of the test and passage rabbits with a homologous strain of *Treponema pallidum*.

In all experiments there was used freshly obtained suspension of *Treponema pallidum* of Nichols's strain.

Given below are the results of experimental studies in the specific activity of the medicinal preparation of the invention.

Bactericial effect of the drug upon Neisser gonococci

The drug was established to completely inhibit the vital activity of the gonococcal cultures in experiments with the strains of pathogens isolated from 7 female and 5 male patients. None of the experimental test tubes exhibited any growth of gonococcal culture, whereas all the control test tubes demonstrated their vigorous growth.

Treponemicidal activity of the drug

It has been established experimentally that nearly instant motionlessness occurs in treponemes under the effect of the drug of the invention, accompanied by destruction of the syphilitic pathogens till their complete lysis as early as within the initial three minutes of their contact with the drug. As fast as on the first minute of contact there are detected sporadic fragments of the destroyed treponemes, there appear long motionless thinned 'filaments' and 'shadows' resulting from smoothing out of the helices, while the majority of the microslides exhibit aggregation of an amorphous protein substance appearing as small fragments of the lyzed pathogens. A similar destructive effect is exerted by the drug involved upon the treponemes of both the Nichol's strain and No. 8 strain of TsKVI. No differences whatever have been identified in the degree of the treponemicidal activity of the drug against the pathogens isolated directly from the patients suffering from infecting forms of syphilis. The treponemicidal effect is confirmed also in tests with experimentally induced syphilis in rabbits. A total of 120 male rabbits have been used in such tests. 100 percent of the test animals have been protected against syphilitic infection due to preventive treatment of the infected spot with the preparation within 15 minutes to 3 hours after application of the inoculative material to the scarified scrotal skin of the test rabbits. At the same time there have been obtained positive results of syphilis prevention upon intracutaneous infection of the test rabbits with a mixture of a suspension of treponemes in an isotonic NaCl solution taken in the same volumetric ratios.

Reliability of preventive protection of the test rabbits against syphilis is judged both by the absence of clinical manifestations of the disease in the animals and the negative serologic tests for syphilis within a follow-up period from 4 to 12 months and by the negative results of transplanting the popliteal lymph nodes from the test rabbits to the indicator rabbits in two serial passages, i.e., first from the test animals to the first-passage indicator rabbits, and then from the latter to the second-passage indicator rabbits. The positive results of reinoculation of both the test and passage animals with a homologous strain of *Treponema pallidum*.

Prevention of the test animals against syphilis upon intracutaneous infection gives evidence that a ten-minute exposure for contact of the drug with the treponemes is quite sufficient for complete inhibition of vital activity of the syphilitic pathogen. On the other hand this can be considered as the demonstration of stability of the drug in a protein medium, that is, the tissues of the rabbits organisms.

Effect of the drug on *Trichomonas vaginalis*

High protistocidal activity of the drug has been established in vitro experiments with 16 strains of vaginal trichomonads isolated from patients suffering from urogenital trichomoniasis (13 females and 3 males), a total of 256 microspecimens being subjected to examination. Vaginal trichomonads are found to get immobilized and to lose their flagellas upon being exposed to the effect of the drug as early as on the first minute of exposure. It is within the next 2 or 3 minutes that complete disintegration of this protozoan occurs, and only some individual microspecimens exhibit sporadic motionless nondisintegrated trichomonads devoid of the flagellas.

The drug has been tested for safety by determining its acute and chronic toxicity, local irritating effect on the skin and mucosa, allergizing and immunogenic properties. There has been studied also pharmacokinetics of the drug upon topical administration and application to mucosa.

Acute toxicity of the drug has been determined on four animal species. There were used in four runs of experiments a total of 150 albino mice having an average mass of 18.5 g. 18 albino rats (165 g), 18 rabbits (3000 g), and 12 Guinea pigs (400 g). A single dose of the drug under test was calculated proceeding from a future drug application for practical aims (0.07 ml per kg body mass of a conventional human being having an average mass of 70 kg).

Taking account of the specificity of the drug practical application (i.e., for smearing the skin and administering into the urethra) toxicity of the drug under consideration has been studied not only by intraperitoneal administration to albino rats and albino mice but also in topical application and intracavitary administration (intravaginal medication in females and intrarectal administration in males) to albino rats, Guinea pigs and rabbits. Visual observation of the state of the experimental animals was carried out from the very instant of application of the drug under test and lasted for 14 days.

Studies of the drug in question for chronic toxicity have been carried out on two species of laboratory animals, i.e., 24 albino rats (170 to 200 g), and on 24 rabbits of the Chinchilla race (2.5 to 3.0 kg). The drug was administered daily for one month. A single dose of the drug was evaluated in the same way as in studying drug's acute toxicity, with due account of its practical application for preventive purposes.

The experimental animals of one of the groups (6 rabbits and 6 rats) were given the drug in the aforementioned dose daily for one month, while the animals of the other test group incorporating the same quantity of the same species were given a subtoxic dose of the drug ten times the therapeutic dose, i.e., 0.7 ml/kg daily within the initial two weeks; beginning with the third week and up to the end of the month the rabbits were given the drug in a dose of 2,1 ml/kg, whereas the rats were given the drug in a dose of 3.5 ml/kg, the latter two doses exceeding the therapeutic dose by 30 and 50 times, respectively. One of the groups of rabbits and rats (six animals of each species) served as the control, the animals of the group being given an isotonic NaCl solution instead of the drug under study. The drug administration route in the experimental animals was maximally approximated to the drug administration techniques in man. Female animals were given the drug intravaginally and intrarectally (one-third of a total dose); besides, the drug was smeared on the dehaired skin of the inner femoral and abdominal surface (two-thirds of a total dose) and rubbed into the skin for one minute; male animals were given the drug intrarectally (one-third of a total dose), and drug was rubbed into the skin of the scrotum, abdomen and inner femoral surface (two-thirds of a total dose).

Throughout the entire period of observation over the experimental animals there were noted their general status, behaviour, dynamics of their mass and rectal temperature. Studies were made in the drug effect on the functions of the CNS, cardiovasular and respiratory systems, as well as on those of the liver, kidneys, endocrine glands, blood, including biochemical studies into the activity of the heart, lungs, liver, kidneys, and endocrine glands. On termination of a monthly course of the drug adminstration the experimental animals were sacrificed, whereupon there were performed histomorphologic examinations of the brain and spinal cord, the heart, lungs, blood vessels, liver, kidneys, pancreas, gonads, blood, and hemopoietic organic (spleen and lymph nodes). In addition, there were examined those areas of the skin and vaginal and rectal mucosa to which the drug had been administered, and the weight coefficients of the internal organs were determined. The body mass and the rectal temperature were measured once a week. Other physiological characteristics were registered before and after the experiment. Biochemical examinations were carried out three times, i.e., prior to the experiment, in two weeks and in one month that is, after the experiment had been terminated.

Chronic toxicity in the test animals was judged by the following indices; external appearance and behaviour; body temperature and mass dynamics; physiological tests (the 'open field' technique, hexenal-induced sleep test, ECG); clinical urine analyses; integral morphological peripheral blood indices; biochemical blood indices (determining total, direct and indirect bilirubin, creatinine, urea, residual nitrogen, aminotransferases, activity of alkaline phosphatase, activity of serum cholinesterase, alpha-amylase, total protein, thymol turbidity test, determining of C-reactive protein); determining the following microelements: potassium, sodium, calcium, chlorides; pathomorphological examinations of the internal organs of the experimental animals.

The functional activity of the CNS was studied using the 'open field' technique by taking notice of the motor activity and behavioural reaction of the experimental rats within a 3-minute period by the number of runs, washes and sets they perform. Besides, the functional status of the CNS was assessed by the duration of a latent period in the hexenal-induced sleep test (by intraperitoneal administration of a 0.7-percent hexenal solution in a dose of 70 mg/kg).

Electrical activity of the heart was registered with the aid of electrocardiograph ELKAR 087 in standard lead II at a tape advance speed of 50 mm/s. Processing of electrocardiograms involved the heart rate value, duration of a complete cardiac cycle R-R, intervals, QRS, QRST and also the voltage value of the Q, R, S, T waves.

Water-excretory and concentratory renal functions were assessed by the volume of the daily diuresis following a water load (5 ml of an isotonic NaCl solution per 100 g animals' body weight) and by the specific mass of urine. The nitrogen-excretory function of the kidneys was assessed by the concentration of residual nitrogen, urea, as well as by the blood serum creatinine content.

Blood specimen was taken from the several tail end of the test rats and from the marginal auricular vein of the test rabbits. Hemoglobin was determined photometrically according to a unified hemoglobin-cyanide method using a standard set of reagents. The erythrocyte count was determined photometrically with the FEK-56M apparatus; first there had been established photometrically and by determining an absolute amount or erythrocytes in Goryaev's counting chamber that 0.1 unit of an optic density corresponds to 1.217 million erythrocytes per 0.01 ml blood. Erythrocyte sedimentation rate, total leukocyte count and leukocytic picture were determined. The blood content of bilirubin, creatinine, urea, aminotransferases, total and C-reactive protein was determined by the unified methods using standard sets of reagents.

Specimens of internal organs for pathomorphological examinations were taken from decapitated test animals (rats), or from those sacrificed by means of aeroembolism (rabbits). The sampled specimens were fixed in a 10-percent neutral formalin solution and stained with hematoxylin-eosin. Simultaneously there were measured the mass and weight coefficients of internal organs.

Local irritating effect of the drug on the skin and mucosa was studied in three runs of experiments. In the first run there were employed 35 Guinea pigs and 30 rabbits of the Chinchilla race to which the preparation was administered by being rubbed into the dehaired skin areas and medicated into the conjunctival sac or both eyes (once and twice a day for 10 days).

In the second run of experiments (8 rabbits) there was studied local irritating effect of the drug on the mucosa of the animals' eyes when given in a concentration ten times that recommended for preventive purposes. Likewise the first run of experiments the drug was instilled in both eyes one or twice a day at 2 or 3-hour interval for 10 days.

In the third run of experiments (aimed at studying chronic toxicity) the local irritating effect of the drug was studied under the conditions to a maximum extent approximating the practical routine of its application. The drug was administered daily to the test rabbits (12 animals) and the test albino rats (12 animlas) by way of application to the skin and through the vagina (in females) and the rectum (in males) within a period of one month.

Apart from daily observation of the experimental animals' behaviour and of the reaction on the part of the skin and mucosa, the skin and mucosal areas that had been medicated with the drug were removed for histologic examinations upon termination of the experiments.

The allergizing effect of the drug was studied on Guinea pigs, since these animals proved to be the optimum subject for artificial sensitization (Ado A. D., 1970). The animals of the experimental groups were given the drug daily for six days either by smearing the skin with the preparation or by injecting it with a syringe intracavitary (i.e., intravaginally to females and intrarectally to males). The drug doses administered were either therapeutic (0.07 ml/kg) or exceeded the therapeutic ten or fifteen times (0.7 and 1.2 ml/kg, respectively). The challenge dose equal to the summary sensitizing one, was administered in 21 to 23 days. A total of 24 Guinea pigs were used in the experiments (four groups containing six animals each, and one control group). The degree of the allergizing effect was judged visually by such symptoms as hyperemia, microvesiculation, skin and mucosa infiltration, inadequate behaviour of the test animals, disturbed gait, tremor, etc.), as well as by the results of laboratory immunologic tests, i.e., leukocyte agglomeration reaction, leukopenic test, thrombocytopenic index and variation of the number of eosinophils and basophils in the peripheral blood.

According to the procedure mentioned above increased percentage of leukocyte agglomeration over 30, reduced leukocyte count by 1000 per cubic millimeter of blood, increase in the thrombocytopenic index by more than 22 percent, as well as eosino-basophilia were considered as manifestation of sensibilization to the drug.

Effect of the drug and of its active principle on the immune system of the test animals was studied on 24 rabbits in the course of tests for chronic toxicity (four groups of six test animals in each, one of them being the control). Immunologic examinations were carried out twice: first there was determined an original level of indices, and one month later, that is, upon termination of the drug administration in a therapeutic and subtoxic dose, and its active principle administration in a subtoxic dose. The following tests characterizing the T- and B-links of immunity, as well as nonspecific protection factors were carried out: quantitative determination of the level of immunoglobulins of classes G, A and M in the blood serum (using the radial immunodiffusion after Mancini, 1965), change in the number of lymphocytes and monocytes, titre of the blood serum complement (by the colorimetric method), titre of heterophilic agglutinins (by Paul-Bunnel test), amount of C-reactive protein and total blood serum protein, histological examinations of the spleen and popliteal lymph nodes.

Since the drug is aimed at topical application (to the skin and mucosa), it is important to determine whether the drug may be absorbed from the skin and mucosa or be engaged in the metabolism of the organism. The drug content of the blood was measured by a highly sensitive gas-liquid chromatography method enabling the drug concentration of $10^{-6}$ to $10^{-9}$ g/ml to be determined.

The numerical data thus obtained were processed statistically in the ES-1045 computer.

The results of the aforementioned experiments were as follows.

Minimum toxic manifestations under conditions of an acute experiment involving intraperitoneal drug administration to albino mice were observed at a dose of 8.32 ml/kg, while the maximum ones, at a dose of 20.0 ml/kg body weight of the test animals. The obtained data on studies of acute toxicity of the preparation were processed statistically using the method of B. M. Shtabskoi and associates (1980). $LD_{50}$ for albino mice given the drug intraperitoneally equalled 9.81 ml/kg (9.67 to 9.94) which made it possible to classify the drug as a relatively safe one, according to toxicity classification after K. K. Sidorov, which proved to be the lowest possible degree of toxicity (N. F. Izmerov and associates, 1977).

The results of studies into the drug chronic toxicity give evidence that its daily administration within one month in therapeutic and subtoxic doses produces no harmful effect on the functional state of the organs and systems of the test rabbits' and albino rats' organism. The level of the studies characteristics obtained upon completion of the experiments either corresponded to the initial data or agreed with the similar indices obtained in the comparison (control) group and did not come out of the limits of variations of the physiological norm in the given species of animals as cited by I. P. Zapadniuk and associates (1983), Somewhat higher level of direct and indirect bilirubin in the blood serum ($P>0.05$), as well as somewhat increased activity of aminotransferases ($P>0.05$) noted in both groups of the animals (rabbits and rats) that were given the drug in a subtoxic dose, could be considered as a certain tendency towards a negative effect of a prolonged administration of subtoxic doses on the hepatic function. Pathomorphologic examinations of internal organs of the experimental and control animals of both species revealed no pronounced changes whatever upon administration of both the drug and its active principle.

It has been established experimentally that the drug produces no local irritating effect when applied to the skin or injected intracavitary (i.e., intravaginally and intrarectally) in test rabbits and rats. Morphological examination of the skin areas taken from the test rabbits and rats after smearing such areas with the durg for one month revealed no changes whatever. Nor were revealed any disturbances of the histological structure of the vaginal mucosa (the place of the durg administration to females) and of the rectal mucosa (the place of the drug administration to males). Single and twice-repeated drug adminstration in a therapeutic concentration to the conjunctival sac of both eyes of the test rabbits and Guinea pigs was accompanied by a transient (1 to 2 minutes) lacrimation and by slight reddening of the conjunctival mucosa.

Drug administration to the conjunctival sac of the test rabbits in a dose, wherein the concentration of an antiseptic exceeded the therapeutic one ten times was attended by more pronounced hyperemia of the ocular mucosa and longer duration of this reaction (up to 1.5 to 3 hours). Examination of the histostructure of the eye tissues in the test animals demonstrated that the changes revealed were functional in nature both upon drug administration in a therapeutic concentration and in a concentration exceeding the latter ten times. No manifestations of the destructive nature in the mucosa components were revealed.

Thus, testing for local irritating effect of the drug in three animal species revealed its absence upon drug adminstration to the skin, and to the ocular vaginal and rectal mucosa of the experimental animals.

Studies into the allergizing effect of the drug on 24 Guinea pigs have demonstrated that the drug administration in the therapeutic doses is not attended by any systemic reactions of the test animals, changes in the blood picture and that the cell tests in the course of in vitro experiments remain unchanged. It has been established at the same time that the drug doses exceeding the therapeutic dose ten times and more may to a certain extent cause the development of the symptoms of allergic manifestations, which is charaterized by an increase in leukocyte agglomeration by more than four times, reduction of the leukocyte count by 1.5 thous. per cubic millimeter of blood, increased thrombocyte percent up to 70, and the eoisnophil content increased more that fourfold ($P < 0.05$).

When administered in a therapeutic and even in subtoxic dose the drug produces no effect on the immunity mechanism, i.e., it does not change the number of immunocompetent cells and their functions, especially the synthesis of the main class of antibodies. Nor have been revealed any symptoms of inhibition of nonspecific factors of the animals' organism protection. The results of histologic examinations of the spleen and lymph nodes, wherein no macrophage and lymphoid infiltration and plasmocytic reaction were noticed, to a certain degree confirm the results of immunologic tests.

The drug is equally absorbable upon being applied both to the skin and to the mucosa of the test rabbits. However, absorption through the skin occurs at a slower rate and in a lower amount than through the mucosa. It has also been revealed that though the drug is absorbed through the mucosa at a relatively faster rate than through the skin, yet the absorption process proceeds rather slowly.

Experimental studies have corroborated high specific activity of the drug, according to the invention, against the pathogens of syphilis, gonorrhea and trichomoniasis.

Studies of a harmful effect produced by the drug on the organism of laboratory animals have shown that, according to the results of tests for acute toxicity the drug may be qualified as a relatively safe, while its prolonged administration in the therapeutic doses and even in the subtoxic doses is not attended by any marked harmful effect on the organs and systems of the experimental animals.

The results of preclinical trials of the drug have demonstrated that the drug proves to be most effective for prevention of venereal diseases when used in a liquid medicinal form of the following composition (in mass percent):

| | |
|---|---|
| paranitro-alpha-chlorocinnamic aldehyde of the following formula: 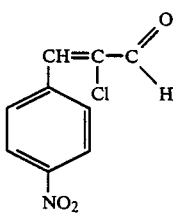 | 0.3 |
| dimethylsulphoxide | 5.0 |
| polyethyleneglycol having a molecular mass of 400 | to make up 100 |

It is recommended that for prevention of venereal diseases and treatment of urogenital trichomoniasis in women the drug be used in a liquid form dispensed in aerosol containers under pressure and have the following composition (in mass percent):

| | |
|---|---|
| paranitro-alpha-chlorocinnamic aldehyde of the following formula: 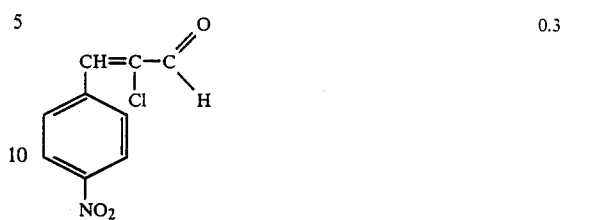 | 0.3 |
| dimethylsulphoxide | 5.0 |
| polyethyleneglycol having a molecular mass of 400 | 10.0 to 30.0 |
| surfactant | 3.0 to 6.0 |
| water | to make up 100.0 | and a propellent in an amount of 3 to 10 percent of a total mass of the ingredients.

Clinical trials of the present medicinal preparation as a remedy for individual prevention of venereal diseases have been studied at the major dermato-venereological institutions in the Soviet Union. The drug has been evaluated also at the stations of individual prevention of venereal diseases, where those who have applied for medical aid have been given preventive aid by the medical personnel of such stations, as well as by dispensing the drug to those persons who practised irregular sexual intercourse. It has been established that no cases of infection with syphilis, gonorrhea or trichomoniasis have been revealed in the men under observation who have had sporadic sexual intercourse and have made use of the drug. Nor have been noted any symptoms of toxic, local irritating or allergizing effect of the drug on patients' organism.

The results of treatment of 105 patients for urogenital trichomoniasis using a therapeutic scheme involving the use of the present medicinal preparation administered in an amount of 1.5 to 10 ml twice a day for 5 to 7 days have shown high therapeutic protistocidal efficiency of the drug manifested in a complete etiological and clinical recovery of the patients. No relapses of trichomoniasis were revealed upon a prolonged (for 3 months) follow-up observation period of the treated patients, nor were noted any side effects.

What we claim is:

1. A medicinal preparation comprising an effective amount of an active principal sufficient to prevent venereal diseases and for treatment of urogenital trichomoniasis which is comprised of a synergistic mixture of paranitro-alpha-chlorocinnamic aldehyde of the formula:

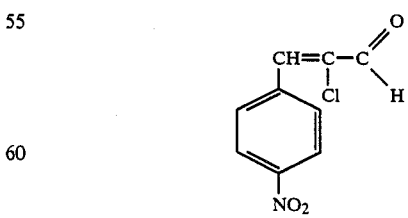

dimethylsulphoxide and the pharmaceutical excipient polyethylene glycol.

2. A medicinal preparation as claimed in claim 1, which comprises polyethyleneglycol having a molecular mass of 400 as the pharmaceutical excipient.

3. A medicinal preparation as claimed in claim 2 in a liquid form, which comprises the aforesaid ingredients in the following ration in mass percent:

| | |
|---|---|
| para-nitro-alpha-chlorocinnamic aldehyde of the aformentioned formula | 0.3 |
| dimethylsulphoxide | 5.0 |
| polyethyleneglycol with a molecular mass of 400 | to make up 100 |

4. A medicinal preparation as claimed in claim 2 in a liquid form dispensed in aerosol containers under pressure, which comprises additionally a surfactant and water, its ingredients being taken in the following ratio in mass percent:

| | |
|---|---|
| para-nitro-alpha-chlorocinnamic aldehyde of the aformentioned formula | 0.3 |
| dimethylsulphoxide | 5.0 |
| polyethyleneglycol with a molecular mass of 400 | 10 to 30 |
| surfactant | 3.0 to 6.0 |
| water | to make up 100 | as well as a propellant taken in an amount of 3 to 10 percent of a total mass of the ingredients.

5. A method for treating urogenital trichomoniasis in a subject which comprises applying to the mucosa of the genitalia of said subject, a therapeutically effective amount of the medicinal preparation of claim 1.

6. A method of treating urogenital trichomoniasis in a subject which comprises applying to the mucosa of the genitalia of said subject, a therapeutically effective amount of the medicinal preparation of claim 2.

7. A method of treating urogenital trichomoniasis in a subject which comprises applying to the mucosa of the genitalia of said subject, a therapeutically effective amount of the medicinal preparation of claim 3.

8. The method of claim 5, wherein the medicinal preparation is applied in a dose of from about 1.5 to about 10 ml.

9. The method of claim 8, wherein the medicinal preparation is applied in a dose of from about 1.5 to about 10 ml. per day, twice a day, over a period of from about 5 to about 7 days.

* * * * *